United States Patent
Muraki

(10) Patent No.: US 8,687,195 B2
(45) Date of Patent: Apr. 1, 2014

(54) OPTICAL MEASUREMENT APPARATUS AND CHIP LIFETIME JUDGMENT METHOD

(75) Inventor: Yosuke Muraki, Tokyo (JP)

(73) Assignee: Sony Corporation, Tokyo (JP)

( * ) Notice: Subject to any disclaimer, the term of this patent is extended or adjusted under 35 U.S.C. 154(b) by 38 days.

(21) Appl. No.: 13/568,901

(22) Filed: Aug. 7, 2012

(65) Prior Publication Data

US 2013/0038878 A1     Feb. 14, 2013

(30) Foreign Application Priority Data

Aug. 11, 2011 (JP) ................................. 2011-175990

(51) Int. Cl.
    *G01N 21/59*     (2006.01)
(52) U.S. Cl.
    USPC ........... 356/436; 356/237.4; 356/73; 356/338
(58) Field of Classification Search
    USPC ............. 356/436, 335–343, 237.1–237.5, 73; 324/750.03, 642, 754.31, 762.01
    See application file for complete search history.

(56) References Cited

U.S. PATENT DOCUMENTS

| | | | |
|---|---|---|---|
| 6,416,413 B1* | 7/2002 | Yoo | 463/42 |
| 8,482,731 B2* | 7/2013 | Muraki | 356/342 |
| 2006/0192940 A1* | 8/2006 | Phi-Wilson | 356/73 |
| 2006/0239862 A1* | 10/2006 | Nakajima et al. | 422/100 |
| 2009/0231025 A1* | 9/2009 | Wang et al. | 327/543 |
| 2010/0314555 A1* | 12/2010 | Muraki | 250/459.1 |

FOREIGN PATENT DOCUMENTS

JP     2010-054492     3/2010

* cited by examiner

*Primary Examiner* — Hoa Pham
(74) *Attorney, Agent, or Firm* — K&L Gates LLP

(57) ABSTRACT

An optical measurement apparatus including a light irradiation portion configured to irradiate light onto a sample flowing through a flow path in a detachable chip; a light detection portion configured to detect optical information emitted from the sample when irradiated with the light by the light irradiation portion; and a judgment portion configured to judge an exchange period of the chip based on the optical information detected by the light detection portion.

7 Claims, 6 Drawing Sheets

Flow 1

Flow 2

Flow 3

Flow 4

Flow 5

Case where 10,000eps*60sec*5times is set as lifetime per chip

OPTICAL MEASUREMENT APPARATUS AND CHIP LIFETIME JUDGMENT METHOD

CROSS REFERENCES TO RELATED APPLICATIONS

The present application claims priority to Japanese Priority Patent Application JP 2011-175990 filed in the Japan Patent Office on Aug. 11, 2011, the entire content of which is hereby incorporated by reference.

BACKGROUND

The present disclosure relates to an optical measurement apparatus and a chip lifetime judgment method, more specifically, to an optical measurement apparatus including a judgment portion that judges a lifetime of a chip by optically detecting a sample flowing through a flow path in a detachable chip and a chip lifetime judgment method for judging a lifetime of a chip by optically detecting a sample flowing through a flow path in a detachable chip.

In recent years, along with a development of analysis techniques, a technique that causes biological microparticles such as a cell and a microorganism, microparticles such as microbeads, and the like to flow through a flow path to individually measure the microparticles in the flowing process and analyze and dispense the measured microparticles, and an optical measurement apparatus that uses such a technique are being developed.

As a typical example of such a technique of analyzing or dispensing microparticles using a flow path, an analysis technique called flow cytometry is being technologically improved. In addition, in the flow cytometry, a detachable microchip is starting to be used. For example, a microchip including a flow path through which a sheath fluid can flow and a microtubule for introducing a sample fluid into the sheath fluid laminar flow flowing through the flow path is known (see, for example, Japanese Patent Application Laid-open No. 2010-54492).

The technique of analyzing and dispensing microparticles in a flow path as in the flow cytometry is widely used in various fields such as a medical field, a drug development field, a clinical examination field, a food field, an agriculture field, an engineering field, a forensic medicine field, and a criminal identification field. In the medical field in particular, the technique plays an important role in pathology, tumor immunology, transplantation, genetics, regenerative medicine, chemotherapy, and the like.

In the optical measurement apparatus as described above, for improving a measurement accuracy or improving a working efficiency by lessening apparatus cleaning and the like, a detachable microchip, particularly a chip that is disposable after a predetermined period is used in many cases. In actuality, however, a user uses the chip for a long period of time or reuses it after washing it. In addition, since the user judges a lifetime of the detachable chip based on experiences or by instinct, there is a problem that the measurement accuracy of the optical measurement apparatus may be lowered or a defect is apt to occur.

SUMMARY

A method and apparatus capable of prompting a user to exchange a chip during a chip exchange period (hereinafter, also referred to as "chip lifetime") without relying on individual experiences or instinct are being demanded.

In view of the circumstances as described above, there is a need for an optical measurement apparatus and a chip lifetime judgment method for prompting a user to exchange a chip.

According to an embodiment of the present disclosure, there is provided an optical measurement apparatus including: a light irradiation portion configured to irradiate light onto a sample flowing through a flow path in a detachable chip; a light detection portion configured to detect optical information emitted from the sample when irradiated with the light by the light irradiation portion; and a judgment portion configured to judge an exchange period of the chip based on the optical information detected by the light detection portion. With this structure, the chip lifetime (exchange period) can be judged without relying on experiences or instinct of individual users, and such a judgment can be stably made for each chip with less variances. Moreover, it also becomes possible to freely change conditional settings as follows according to a user demand on measurement purposes, target, and the like.

The optical measurement apparatus may further include a chip information recognition portion configured to recognize chip information from an identifier. In this case, the judgment portion may judge the exchange period of the chip based on at least one of the optical information and the chip information. With this structure, a usage condition of the chip can be grasped more accurately.

The optical information may be selected based on a threshold value. With this structure, it becomes possible to remove noises that are apt to cause a judgment error when judging the chip lifetime (exchange period). As a result, the lifetime judgment for each chip can be carried out with ease without variances.

The judgment portion may judge that it is currently the exchange period of the chip when the number of samples calculated based on the optical information reaches a constant value of a maximum count number.

The judgment portion may judge that it is currently the exchange period of the chip when a certain time has passed since it is judged that a large amount of samples have been measured at the same time based on the optical information.

The judgment portion may judge that it is currently the exchange period of the chip when a size of the sample calculated based on the optical information reaches a constant value of a maximum integration value for the sample size.

According to an embodiment of the present disclosure, there is provided a chip lifetime judgment method, including: irradiating light onto a sample flowing through a flow path in a detachable chip; detecting optical information emitted from the sample when irradiated with the light; and judging an exchange period of the chip based on the detected optical information.

Here, the "sample" used in the present disclosure is a substance capable of flowing through a flow path and is, for example, biologically-relevant microparticles such as a cell, microorganism, liposome, DNA, and protein or synthetic particles such as latex particles, gel particles, and industrial particles.

According to the embodiments of the present disclosure, it becomes possible to prompt a user to exchange a chip without relying on experiences or instinct of individual users.

Additional features and advantages are described herein, and will be apparent from the following Detailed Description and the figures.

DETAILED DESCRIPTION

Hereinafter, an embodiment of the present disclosure will be described with reference to the drawings. It should be noted that the embodiment below is an example of a typical embodiment of the present disclosure, and the range of the present disclosure shall not be narrowly interpreted. It should be noted that the descriptions will be given in the following order.

1. Optical measurement apparatus
   (1) Chip
   (2) Light irradiation portion
   (3) Light detection portion
   (4) Electric signal conversion portion/AD conversion portion
   (5) Chip information recognition portion
   (6) Judgment portion
2. Chip lifetime judgment method
3. Flow cytometer <1. Optical Measurement Apparatus>

Figure 1:
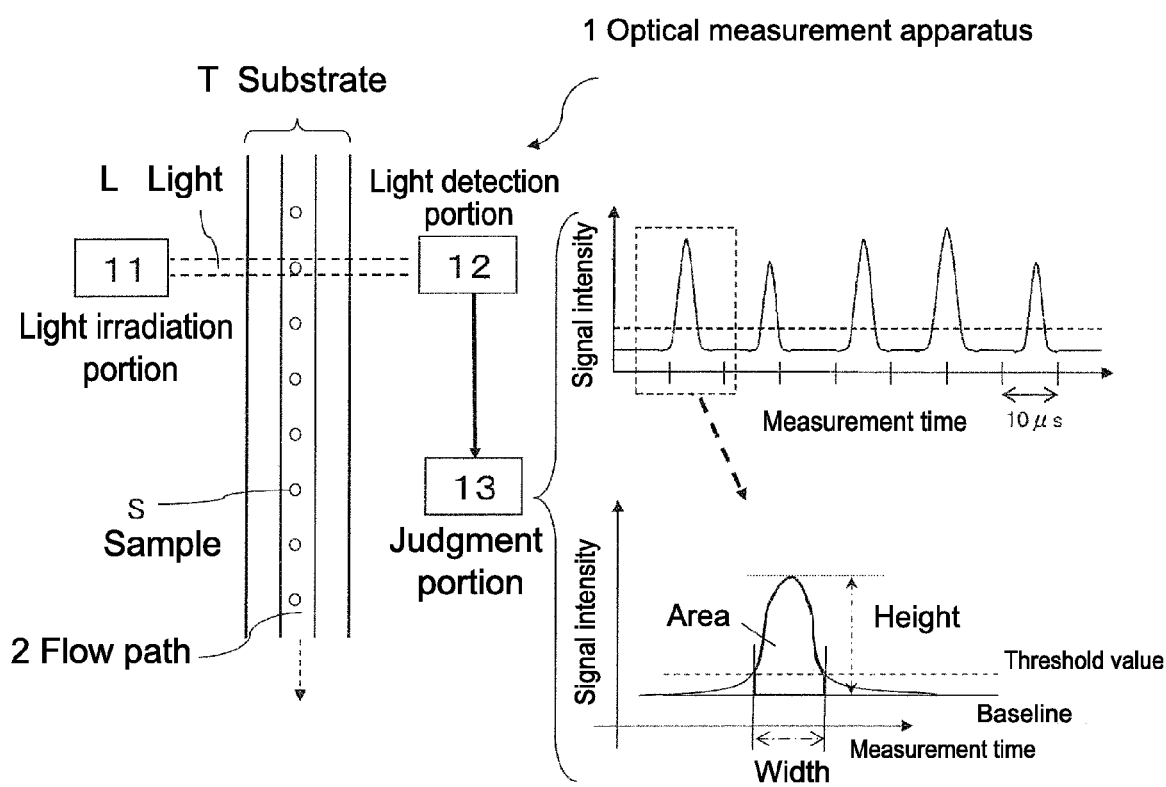
FIG. 1 is a schematic conceptual diagram showing an optical measurement apparatus 1 according to a first embodiment of the present disclosure.
Figure 2:
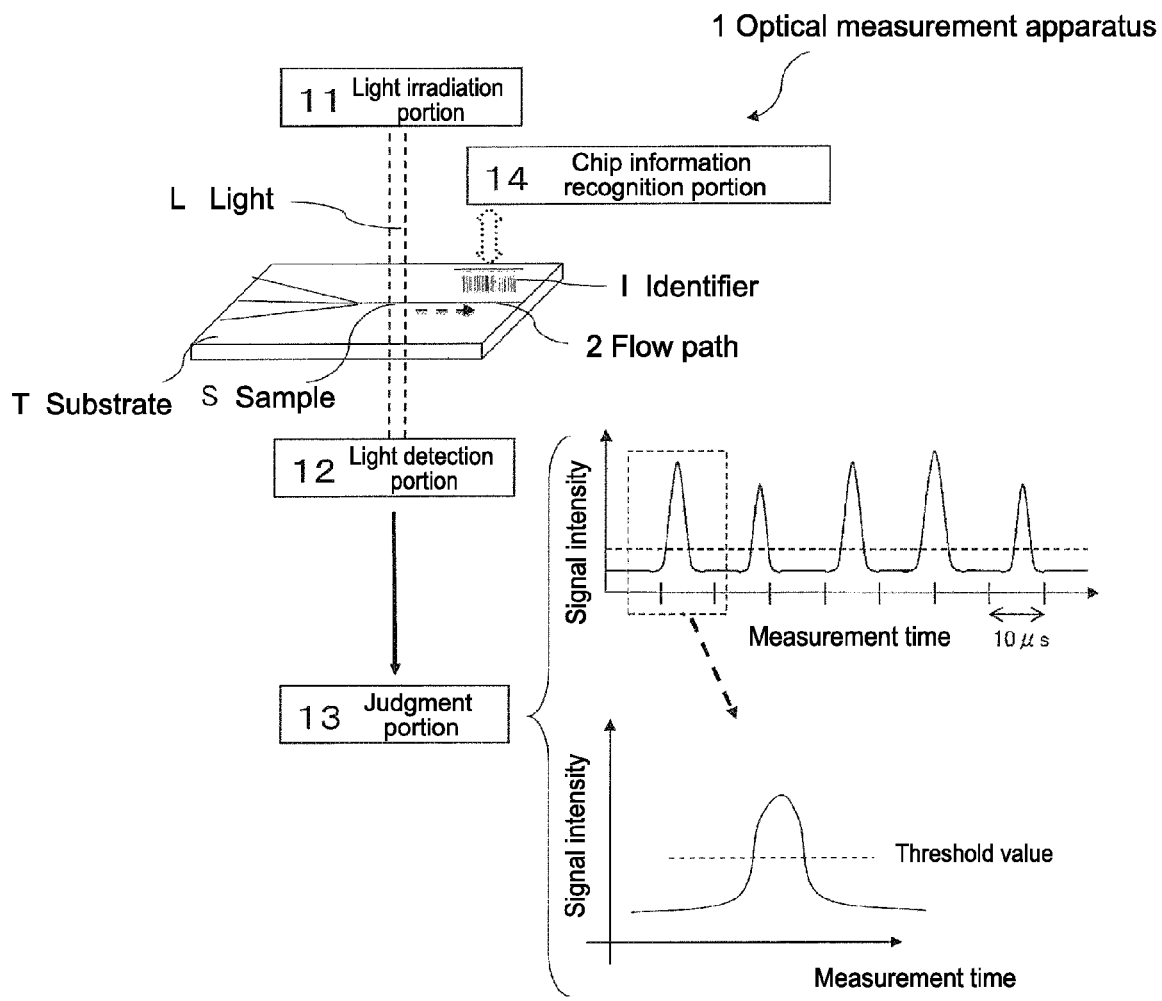
FIG. 2 is a schematic conceptual diagram showing the optical measurement apparatus 1 according to the first embodiment of the present disclosure.

FIGS. 1 and 2 are schematic conceptual diagrams each showing an optical measurement apparatus 1 according to a first embodiment of the present disclosure.

The optical measurement apparatus 1 of the present disclosure includes at least a light irradiation portion 11, a light detection portion 12, and a judgment portion 13 in a rough classification.

A detachable chip (substrate T) including a flow path 2 can be mounted on the optical measurement apparatus 1. When the chip (substrate T) has an identifier I, the optical measurement apparatus 1 may include a chip information recognition portion 14 that recognizes chip information from the identifier I.

The optical measurement apparatus 1 may also include an electric signal conversion portion (not shown) that converts optical information into an electric signal (light pulse) and an AD conversion portion (not shown) that performs an analog-digital conversion. It should be noted that the optical measurement apparatus 1 of the present disclosure may also include a portion that adjusts a laminar flow of the flow path 2 in the chip, a temperature controller, a dispensing portion, and a controller that controls functions of the respective portions. Further, the controller may execute processing that is carried out by the judgment portion, the chip information recognition portion, the electric signal conversion portion, the AD conversion portion, and the like.

According to the present disclosure, it becomes possible to judge a chip exchange period (chip lifetime) without relying on experiences or instinct of individual users and thus prompt the user to exchange the chip. In other words, according to the present disclosure, it becomes possible to automatically calculate and predict a chip usage condition including a chip use frequency and a period of use and prompt the user to exchange the chip that has been or is to be used a certain amount/period or more.

Moreover, since variances in the lifetime judgment per chip can be lessened, the chip exchange can be performed stably and efficiently. Furthermore, it also becomes possible to freely change conditional settings on a chip lifetime according to a user demand on measurement purposes, target, and the like. In addition, the chip lifetime can be judged in real time. As a result, the chip usage condition can be grasped more accurately, and thus running costs in optical measurements can be reduced.

(1) Chip

The optical measurement apparatus 1 of the present disclosure can be equipped with the detachable chip (substrate T) including the flow path 2. A mounting position of the chip is, for example, a position between the light irradiation portion 11 and the light detection portion 12. For example, a vertical-type chip or a horizontal-type chip can be mounted.

Further, it is desirable for the chip to have an identifier I with which chip information can be obtained (see FIG. 2 as one example). A position of the identifier I is not particularly limited. For example, the identifier I may be assigned to a package of the chip, may be attached to the chip, may be incorporated into a body of the chip, or may be detachable.

With this structure, since the chip usage condition of each chip including a use frequency and a period of use can be grasped with ease, the exchange period of each chip can be judged accurately.

Here, examples of the identifier I include a barcode, a data matrix barcode, a high-frequency wave (RFID), a marker, characters, and a shape (concavo-convex shape, protrusion, notch, groove, etc.). The chip information can be obtained from the identifier I via the chip information recognition portion.

The chip information includes information related to a chip lifetime (exchange period). Examples of the chip information include information on a section of each chip, a chip use frequency, a period of use of a chip, an operation condition of an apparatus at a time a chip is used, and a chip use condition at that time.

A storage portion that stores the chip information is not particularly limited and is the identifier I of the chip, a storage portion in an apparatus to be used, a storage portion present in a network, or the like.

A sample S flows through the flow path 2, and light is irradiated onto a predetermined position of the flow path 2 by the light irradiation portion 11 to be described later so that various types of optical information derived from the sample S are obtained by the light detection portion 12.

A width, depth, and cross-sectional shape of the flow path 2 are not particularly limited and can be designed freely as long as a flow path can be formed. An example of the flow path 2 is a micro flow path having a width of 1 mm or less (more specifically, width of 10 μm or more and 1 mm or less).

It should be noted that when the flow path 2 formed in the chip (substrate T) is adopted, it is desirable to form the surface of the flow path 2 by a transparent material.

It is desirable for the chip to have a structure that forms the flow path 2 by a plurality of substrates as shown in FIG. 1, for example.

Further, a chip in which a flow path at substantially the center for injecting a sample fluid is sandwiched by two flow paths for injecting a sheath fluid and joins the flow path 2 as shown in FIG. 2 may be used. With this structure, a sheath fluid laminar flow and a sample fluid laminar flow are formed so that the sample S flows through the flow path 2. In the case of such a chip, an optical measurement is started by causing the sheath fluid to flow first after setting the chip in the optical measurement apparatus and causing the sample fluid to flow next.

The substrate as the chip can be formed by wet etching, injection molding, cutting, and the like with respect to a substrate layer. The material of the substrate is not particularly limited and can be selected as appropriate in consideration of a detection method, processability, durability, and the like. The material only needs to be a material having heat resistance, optical transparency, and the like and selected based on a desired optical analysis. Examples of the material include glass and various plastics (polypropylene, polycarbonate, cycloolefin polymer, polydimethylsiloxane, etc.).

(2) Light Irradiation Portion

The light irradiation portion 11 of the present disclosure irradiates light onto the sample S flowing through the flow path 2 of the detachable chip.

The light irradiation portion 11 only needs to use a light source corresponding to a desired type of light. The type of light irradiated from the light source is not particularly limited, but for positively causing fluorescent light or scattering light to be emitted from the sample S, it is desirable for the light to be light that has a constant optical direction, wavelength, and optical intensity. Examples of the type of light include a laser and an LED. When the laser is used, the type thereof is also not particularly limited, and one or two types or more selected from an argon ion (Ar) laser, a helium-neon (He—Ne) laser, a dye laser, a krypton (Kr) laser, and the like can be combined freely.

(3) Light Detection Portion

The light detection portion of the present disclosure detects optical information emitted from the sample S when irradiated with light by the light irradiation portion 11.

The light detection portion 12 is not particularly limited as long as it can detect optical information, and a well-known light detector can be freely selected and used.

For example, a fluorescence measurement device, a scattering light measurement device, a reflected light measurement device, a diffracted light measurement device, an ultraviolet spectrometer, an infrared spectrometer, a raman spectrometer, a FRET measurement device, a FISH measurement device, or the like can be used. Further, various other spectrum measurement devices, a so-called multichannel light detector in which a plurality of light detectors are arranged in an array, or the like can also be used. One or two or more types selected from those above can be freely combined and used. The optical information emitted from the sample S can be obtained by combining the light irradiation portion 11 and the light detection portion 12 as described above.

Further, the setting position of the light detection portion 12 is not particularly limited and can be designed freely as long as the optical information emitted from the sample S can be detected. For example, as shown in FIGS. 1 and 2, the light detection portion 12 may be positioned on the other side of the light irradiation portion 11 while sandwiching the flow path 2.

(4) Electric Signal Conversion Portion/AD Conversion Portion

The optical measurement apparatus 1 of the present disclosure may additionally include an electric signal conversion portion (not shown) that converts the optical information into an electric signal. With this structure, a peak (light pulse) by a signal intensity can be obtained.

The electric signal obtained by the conversion can further be AD-converted by an AD conversion portion (not shown). After that, based on the digital data, a histogram may be extracted by an analysis computer and software in a numerical processor or the like to perform an analysis (digital waveform processing etc.).

The optical information detected by the light detection portion 12 can be made a pulse (pulse shape) as shown in FIGS. 1 and 2, for example, by a digital waveform processor (not shown). A peak height, a peak width, and a peak area/volume calculated from the height and width can be calculated based on the pulse shape, baseline, and threshold value. It should be noted that the threshold value can be changed as appropriate by the judgment portion to be described later.

Data on the number of light pulses, the number of light pulses having a height exceeding a threshold value, and a height, width, area, and the like of each pulse can be obtained based on the optical information by the CPU, processor, and the like as described above.

(5) Chip Information Recognition Portion

It is desirable for the optical measurement apparatus 1 of the present disclosure to additionally include a chip information recognition portion 14. The chip information recognition portion 14 may be connected to the optical measurement apparatus 1 via a network, a communication cable, or the like. The chip information recognition portion 14 is an apparatus capable of recognizing the identifier I as chip information by a mechanical recognition or the like (see, for example, FIG. 2). The chip information recognition portion 14 only needs to be set such that it can recognize the identifier I.

An example of the method for recognition includes photographing and reading the identifier I (e.g., barcode, characters, and 3D shape) by the chip information recognition portion 14 (e.g., barcode reader and CCD camera) to thus obtain image data of the identifier I.

As an example, data of the identifier I attached to a package of the chip may be obtained by an image recognition apparatus such as a CCD camera connected to or incorporated into a personal computer and the like. Moreover, when the chip is equipped in the optical measurement apparatus, data of the identifier I in the chip may be obtained by the image recognition apparatus or the like.

Further, as the shape of a notch or the like formed in the chip is brought into contact with or bonded to a sensor of the chip information recognition portion 14, the identifier is recognized, and data thereof is obtained.

The obtained data of the identifier is converted by the CPU or the like according to a certain rule to become chip information of digits, characters, symbols, and the like.

Furthermore, as the method for the recognition, in a case where the identifier I set to the substrate is a high frequency wave (RFID) or the like, the chip information recognition portion 14 including a wireless function can obtain chip information stored in the identifier.

The chip information recognition portion 14 can collate the chip information obtained from the identifier of the chip with the data of the chip information stored in a storage portion 28 to be described later or the like and judge whether the mounted chip has been used.

Moreover, the chip information such as information on a usage condition (use frequency, period of use, etc.) of each chip can also be stored in a storage portion provided in the optical measurement apparatus, network, and the like.

As a result, even when the power of the apparatus is turned off, the judgment on the chip exchange period can be made after reboot. In addition, in a case where a network system is structured by a plurality of apparatuses, the judgment on the chip exchange period can be made even for a chip that has been used in a different apparatus. Moreover, it is also possible to update and store new chip information that has been obtained during the measurement.

(6) Judgment Portion

The judgment portion 13 of the present disclosure judges the chip exchange period based on the optical information detected by the light detection portion 12 (see, for example, FIGS. 3 to 8).

Figure 9:
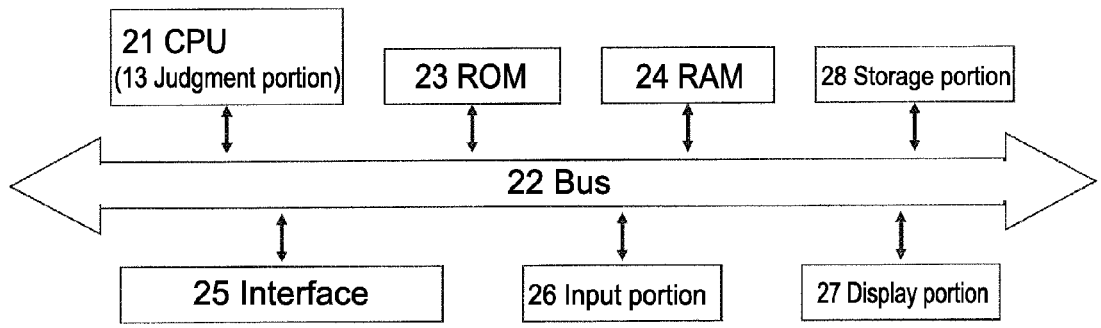
FIG. 9 is a block diagram showing a structure of a judgment portion.

FIG. 9 shows an example of a schematic structure of the judgment portion 13. The judgment portion 13 includes at least a CPU (Central Processing Unit) 21. The judgment portion 13 is capable of being structured by connecting various types of hardware to the CPU via a bus 22. It should be noted that the CPU and the various types of hardware may use various hardware resources equipped in the optical measurement apparatus.

As the hardware, at least a ROM (Read Only Memory) 23, a RAM (Random Access Memory) 24 that is used as a working memory of the CPU 21, and an interface 25 are used. In this embodiment, an input portion 26 to which a command corresponding to a user operation can be input, a display portion 27, and a storage portion 28 are also used.

The hardware capable storing items, such as the ROM 23 and the storage portion 28, stores a program for executing processing of a "chip lifetime judgment method" to be described later (hereinafter, also referred to as "chip lifetime judgment program"). Connected to the interface 25 are the light irradiation portion 11, the light detection portion 12, the electric signal conversion portion, the AD conversion portion, and the chip information recognition portion 14.

The CPU 21 is capable of developing, when a command to judge a chip lifetime (exchange period) is input by the input portion 26, an insertion of a chip, or the like, the chip lifetime judgment program stored in the ROM 23 or the like in the RAM 24 and functioning as a wavelength analysis portion, an individual identification processor, or the like. The wavelength analysis portion is capable of processing optical information and analyzing the number of peak apexes, width, and area/volume of light pulses, for example. Further, the chip information recognition portion 14 is capable of carrying out mechanical recognition processing of chip information, conversion processing for converting identifier data into chip information, and the like.

The CPU 21 is also capable of controlling the apparatus based on the optical information and the chip information.

The CPU 21 is also capable of storing the information data in the storage portion 28 and using them for a calculation as appropriate.

The judgment portion 13 judges a chip lifetime (chip exchange period) according to the "chip lifetime judgment method" to be described later. Further, it is desirable for the optical information to be converted into digital data.

In general, in a case where a chip is used for a long period of time or reused after being washed, particles are apt to adhere onto the inside of the flow path of the chip to thus cause clogging of the flow path. Moreover, an accumulation that disturbs a sample flow is apt to occur in general, particularly at a flow path change point (e.g., point where flow path becomes long and thin).

In contrast, by the chip lifetime judgment of the present disclosure, it becomes possible to prompt the user to exchange, without relying on experiences or instinct of individual users, the chip before troubles such as clogging and an accumulation of a sample, buffer fluid, and the like occur in the flow path.

Moreover, it is desirable to store in advance various types of conditionally-set threshold data in the storage portion 28 and the like so that analog and digital data on the obtained optical information can be sorted based on the threshold values. As a result, the chip exchange period can be judged more accurately with less variances.

<2. Chip Lifetime Judgment Method>

The chip lifetime judgment method (judgment procedure) of the present disclosure includes at least a judgment procedure for judging the chip exchange period based on optical information derived from the sample S flowing through the flow path 2 in the detachable chip.

More desirably, the method includes a light irradiation procedure for irradiating light onto the sample S flowing through the flow path 2 in the detachable chip and a light detection procedure for detecting, by the light detection portion 12, optical information emitted from the sample S when irradiated with light by the light irradiation portion 11.

There is the following judgment method as the more-desirable chip lifetime judgment method.

An example of the method is a chip lifetime (exchange period) judgment method including a procedure obtained by combining one or two or more types selected from the following items (a) to (c).

Figure 3:
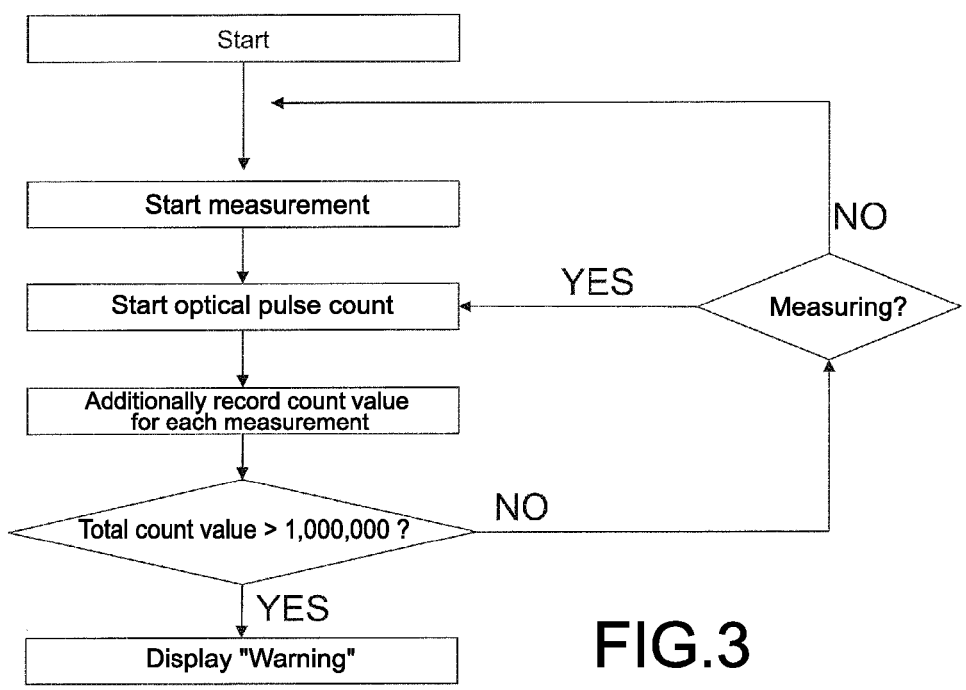
FIG. 3 is a flowchart showing a flow 1 of a chip lifetime judgment method according to the embodiment of the present disclosure.

Specifically, (a) the chip lifetime (exchange period) is judged when the number of samples S calculated based on the optical information reaches a constant value of a maximum count number (see FIG. 3).

Figure 4:
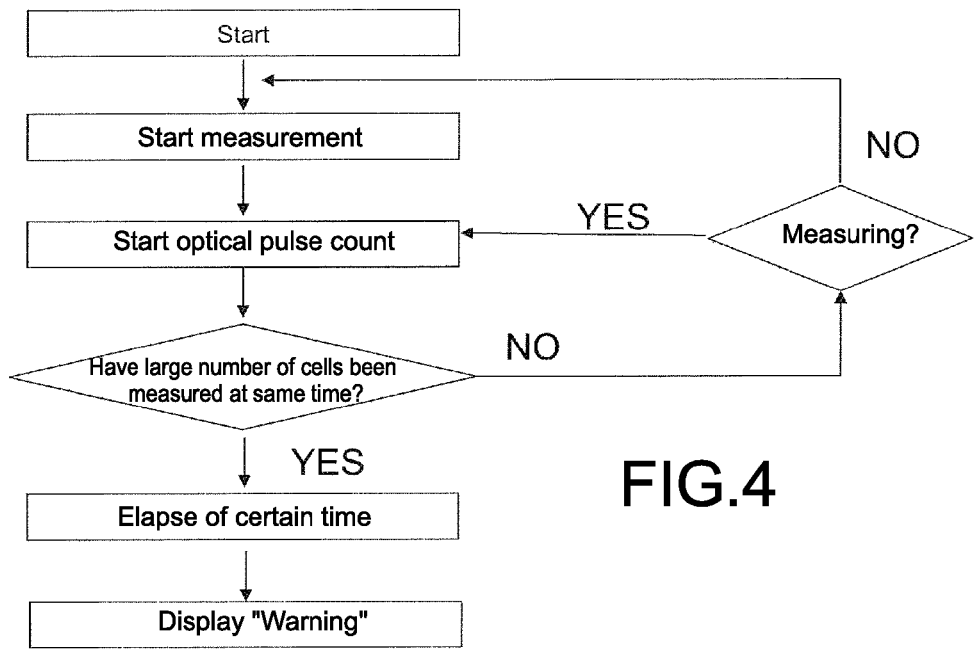
FIG. 4 is a flowchart showing a flow 2 of the chip lifetime judgment method according to the embodiment of the present disclosure.

Further, (b) the chip lifetime (exchange period) is judged after a certain time has elapsed since it is determined that a large number (plurality) of samples S have been measured at the same time based on the optical information (see FIG. 4).

Figure 5:
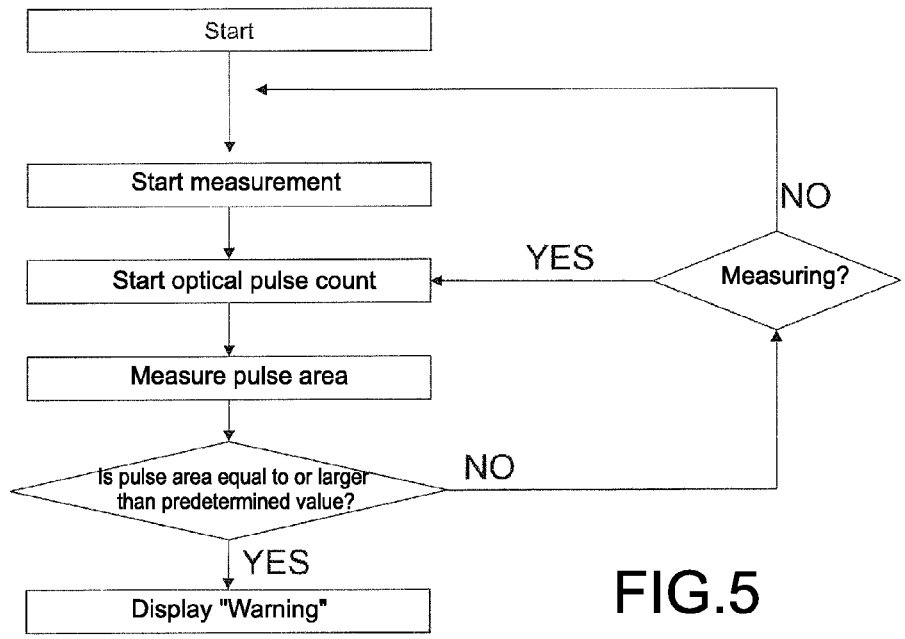
FIG. 5 is a flowchart showing a flow 3 of the chip lifetime judgment method according to the embodiment of the present disclosure.

Furthermore, (c) the chip lifetime (exchange period) is judged when a size of the sample S calculated based on the optical information reaches a constant value of a maximum integration number for the size of the sample S (see FIG. 5).

Using the flow 1 shown in FIG. 3, the case where (a) the chip lifetime (exchange period) is judged when the number of samples S calculated based on the optical information reaches a constant value of a maximum count number will be described.

The judgment portion 13 determines, with one peak derived from optical information emitted from one sample S (cell) in the flow path 2 of the chip after start of the measurement (hereinafter, also referred to as "1 peak reference"), one peak apex as one count. As the 1 peak reference, a mean value of a plurality of peaks to be measured may be used. It should be noted that the count number may be an integer.

Further, conditional settings as in (i) and (ii) below may be set as appropriate, for example.

Figure 8:
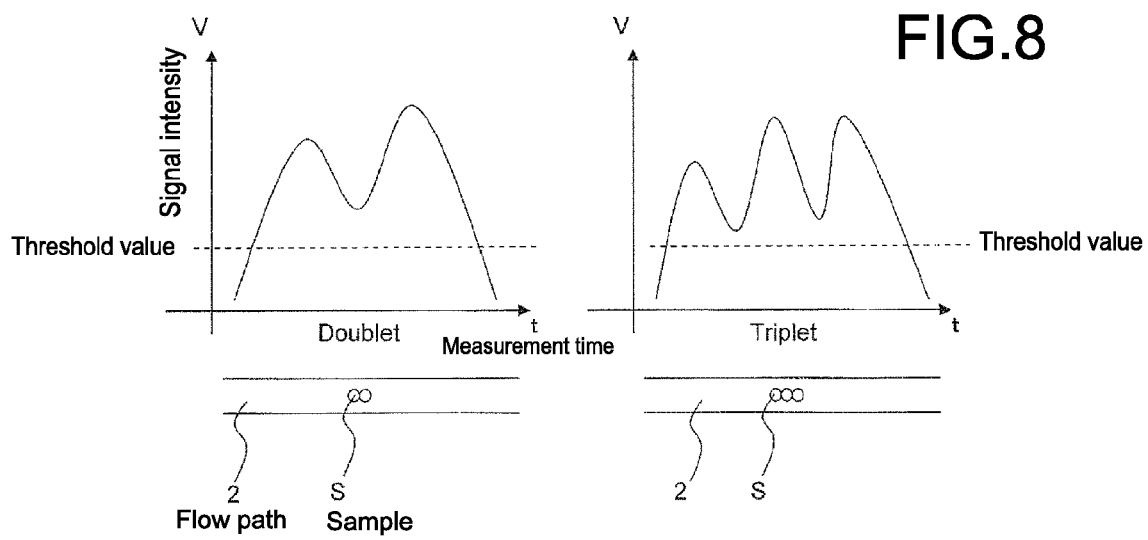
FIG. 8 is a figure-substitution graph showing an example of a state of optical information (pulse signal etc.) in a case where a large amount of 2 samples S come flowing at the same time (cases where number of particles is 2 and 3)

(i) As shown in FIG. 8, a peak having a plurality of peak apexes due to a peak split of the measured peak is selected. In this case, the number of peak apexes of the peak split is counted.

Further, (ii) a peak whose height of one peak that has been measured is higher than that of "1 peak reference" is selected.

The height of the selected peak is divided by the height of the "1 peak reference". The quotient at this time is counted as the number of peak apexes.

Furthermore, it is desirable to set a threshold value for sorting the peaks based on heights. Peaks whose heights are equal to or larger than the threshold value are counted, and peaks whose heights are smaller than the threshold value are not counted. As a result, errors in the peak count due to effects of noises and the like can be lessened.

It should be noted that a situation in which the measured peak exceeds the set threshold value is also referred to as "event".

It is desirable for the judgment portion 13 to store measurement data on the count number (value), measurement time, signal intensity, and the like in the storage portion 28, the RAM 24, and the like. It is also possible to calculate the number of events (event per sec: eps) per unit time (sec) based on the data.

Then, the judgment portion 13 judges that it is currently the chip exchange period when a total count value of the number of peak apexes (cell count number) reaches a constant value (upper limit value) of the maximum count number that has been stored in the storage portion 28 or the like in advance (YES) and causes the display portion 27 to display "Warning". By the display of the warning, the user is prompted to exchange the chip.

When the count value exceeds the "maximum count number", the possibility that clogging will occur in the flow path or the detection accuracy will be lowered becomes extremely high.

Further, the "display" only needs to be understood visually, auditorily, tactually, and the like, and light, audio, vibrations, and the like may be used in addition to an image. Moreover, the display may be made in a network terminal and the like via a network. A means and method therefor are not particularly limited.

Further, the judgment portion 13 is also capable of predicting a reaching time that the count value reaches the maximum count number based on the eps and displaying the reaching time together with a "pre-warning" before the warning.

On the other hand, when it is judged that the total count value has not yet reached the constant value of the maximum count value (e.g., number of events>1,000,000) (NO), the judgment portion 13 further judges whether it is still "measuring".

When judged that it is still "measuring" (YES), the optical pulse count is continued. When judged that it is not "measuring" (NO), a "new measurement" for a new test sample is started.

At this time, the obtained data on the number of peak apexes up to that time, eps, and the like are stored in the storage portion 28 and the like. Accordingly, a cumulative number of the number of peak apexes of the chip (e.g., number of cumulative events) can be used even after the "new measurement". As a result, a warning of a higher accuracy can be displayed.

Using the flow 2 shown in FIG. 4, the case where (b) the chip lifetime (exchange period) is judged after a certain time has elapsed since it is determined that a large number of samples S (cells etc.) have been measured at the same time based on the optical information will be described. Parts that are the same as that of the flow 1 described above will be omitted as appropriate.

The judgment portion 13 judges whether a large number of samples S have passed the measurement portion at the same time in the flow path 2 of the chip after the start of the measurement. When the large number of samples S have passed at the same time, it is highly likely that the concentration of the sample solution being measured is high, and there is a high possibility that clogging will occur in the flow path.

When judged that the size of the measured peak is larger than "one peak of one sample (cell)" (1 peak reference) ("large peak"), the judgment portion 13 judges that the plurality of samples S have passed a predetermined portion of the flow path at the same time.

Here, the comparison between the measured peak and the 1 peak reference only needs to be performed based on a shape of the peak (height, width, and area/volume), desirably the peak area in consideration of a peak split or broad peak depending on a data processing speed or a passage of a large number of samples.

At this time, it is desirable to set, to the judgment portion 13, a threshold value for sorting the measured peaks based on shapes (height, width, area/volume, etc.).

For example, by raising the setting of the threshold value, the fact that numerous samples S have passed at the same time can be displayed as an "emergency warning". On the other hand, by lowering the setting of the threshold value, even the fact that a small number of samples S have passed at the same time can be displayed as the "warning". As a result, since the warning level can be changed according to the level of the number of samples S that pass at the same time, it becomes easy to avoid troubles such as clogging.

Further, a plurality of threshold values may be set so that it becomes possible to set a plurality of warning levels corresponding to the plurality of set threshold values and display at the corresponding warning level.

The judgment portion 13 may also set the number of judgment times in a case where it is judged that the large number of samples S have been measured at the same time and display the "emergency warning" when the number exceeds the set number of judgment times.

As described above, since the possibility of clogging of the flow path becomes high after a certain time elapses since judging that a large number of samples S have been measured at the same time ("large peak") (YES), the judgment portion 13 judges that it is currently the chip exchange period and displays the "warning" on the display portion.

When judged that a large number of samples S have not been measured at the same time (NO), the judgment portion 13 judges whether it is still "measuring". When judged that it is still "measuring" (YES), the optical pulse count is continued. When judged that it is not "measuring" (NO), a "new measurement" on a new test sample is started.

It should be noted that a start point of the "certain time" may be a time point at which a "large peak" is determined A width of the "certain time" can be set in consideration of a size of the "large peak". For example, with a larger "large peak", the width of the "certain time" is set to be shorter, and with a smaller "large peak", the width of the "certain time" is set to be longer. The settings on the start point and the width may be stored in the storage portion 28 and the like in advance.

It should be noted that the "warning" may be displayed immediately without waiting for the certain time to elapse. Further, the "pre-warning" may be displayed when a "large peak" is judged, and the "warning" may be displayed after a certain time elapses after that.

Using the flow 3 shown in FIG. 5, the case where (c) the chip exchange period is judged when a size of the sample S calculated based on the optical information reaches a constant value of a maximum integration number for the size of the sample S will be described. Parts that are the same as that of the flow 1 described above will be omitted as appropriate.

The judgment portion 13 is capable of determining a size of a cell flowing through the flow path 2 of the chip after the start of the measurement from the peak area as described above. The judgment portion 13 calculates the peak area and stores an integration area number in the storage portion 28 or the like. It should be noted that the "peak area" may be substituted by a "peak volume".

At this time, it is desirable to set, to the judgment portion 13, a threshold value for sorting the peaks based on areas (volumes). By setting the threshold value, noises can be removed, and a more-accurate peak area can be obtained.

The "maximum integration number" used herein is a maximum number of an integration of a light pulse and the like and a value at which the possibility that clogging will occur in the flow path or a detection accuracy will be lowered becomes extremely high.

When the sum of peak areas reaches the constant value of the maximum integration number (upper limit value) of the peak area integration that has been stored in the storage portion 28 or the like in advance (YES), the judgment portion 13 judges that it is currently the chip exchange period and displays the "warning" on the display portion 27. By the display of the warning, the user is prompted to exchange the chip. Further, when judged that the sum has not reached the maximum integration number of the peak areas (NO), the judgment portion 13 judges whether it is still "measuring". When judged that it is still measuring (YES), the optical pulse count is continued. When judged that it is not "measuring" (NO), a "new measurement" for a new test sample is started.

Furthermore, two or more selected from (a) to (c) above can be combined. The order of (a) to (c) may be changed as appropriate. The chip exchange period can be judged when two or more selected from (a) to (c) are satisfied.

Figure 6:
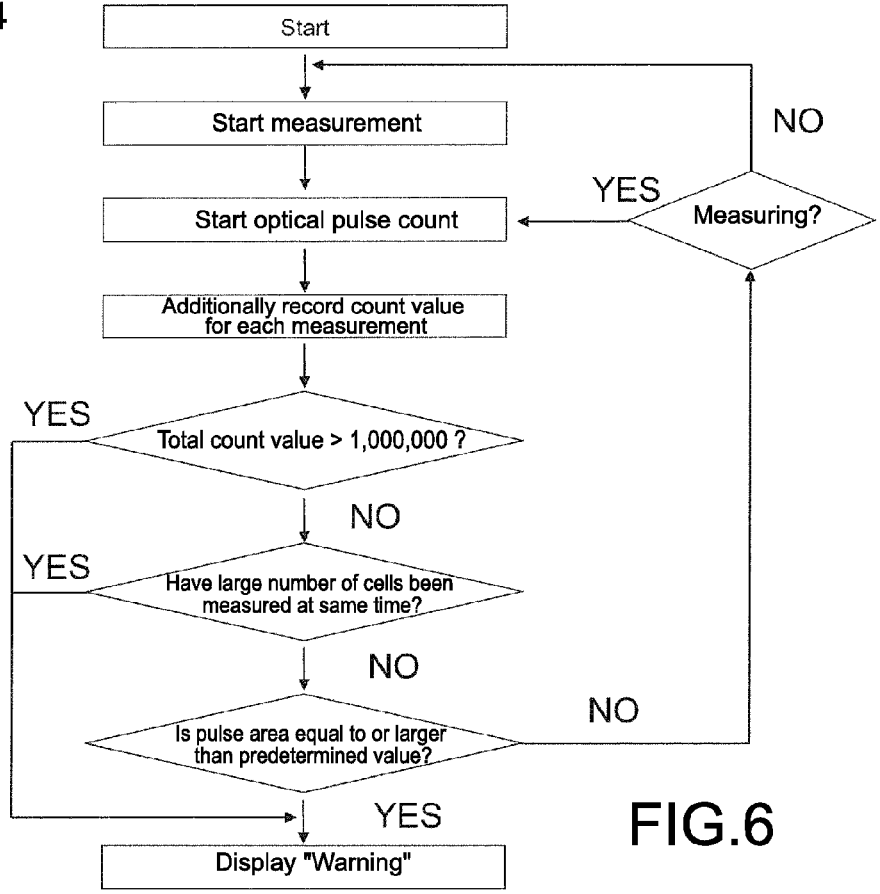
FIG. 6 is a flowchart showing a flow 4 of the chip lifetime judgment method according to the embodiment of the present disclosure.

It is also possible to judge the chip exchange period when any one of (a) to (c) is satisfied (see, for example, FIG. 6). As a result, clogging of the flow path and the like can be prevented more positively.

The judgment portion 13 is capable of calculating the number of peak apexes, peak height, peak width, peak area (volume), and the like based on the optical information. In addition, those values may be integrated, and data thereof may be stored in the storage portion 28 or the like. It should be noted that a predetermined total count value of the number of peak apexes, a predetermined peak area, and a predetermined upper limit value of the peak area integration are stored in the storage portion 28.

The judgment portion 13 judges whether the total count value of the number of peak apexes is equal to or larger than a predetermined total value of the peak apexes (YES or NO). When the value is equal to or larger than the predetermined value, the "warning" is displayed.

When the value is not equal to or larger than the predetermined total value of the peak apexes (NO), the judgment portion 13 then judges whether a large number of samples S have been measured at the same time. Further, the judgment portion 13 judges whether the area is equal to or larger than the predetermined peak area (volume) (YES or NO). When judged to be equal to or larger than the predetermined peak area (volume), the "warning" is displayed.

When judged that the area is not equal to or larger than the predetermined peak area (volume) (NO), the judgment portion 13 may display the "pre-warning". Then, the judgment portion 13 judges whether the value is equal to or larger than the predetermined upper limit value of the peak area integration (YES or NO).

When judged to be equal to or larger than the predetermined upper limit value of the peak area integration (YES), the "warning" is displayed. When judged that the value is not equal to or larger than the predetermined upper limit value of the peak area integration (NO), the judgment portion 13 judges whether it is still "measuring". When judged that it is still "measuring" (YES), the optical pulse count is continued. When judged that it is not "measuring" (NO), a "new measurement" for a new test sample is started.

By using the identifier I and the chip information recognition portion 14, an elapse of time since the chip is mounted on the apparatus can be counted. Moreover, it is possible to judge the chip exchange period when the chip mounting time becomes equal to or larger than a predetermined mounting time and display the "warning" on the display portion.

As an example, when the chip is inserted, the chip information from the identifier I is collated with the chip information stored in the storage portion 28. When the chip is mounted on the apparatus for the first time (YES) as a result of the collation, the optical pulse count is started. On the other hand, when the chip is mounted on the apparatus a plurality of times (NO), the chip exchange period is judged without starting the optical pulse count, and the "warning" is displayed on the display portion. As a result, the chip can be prevented from being used twice.

Figure 7:
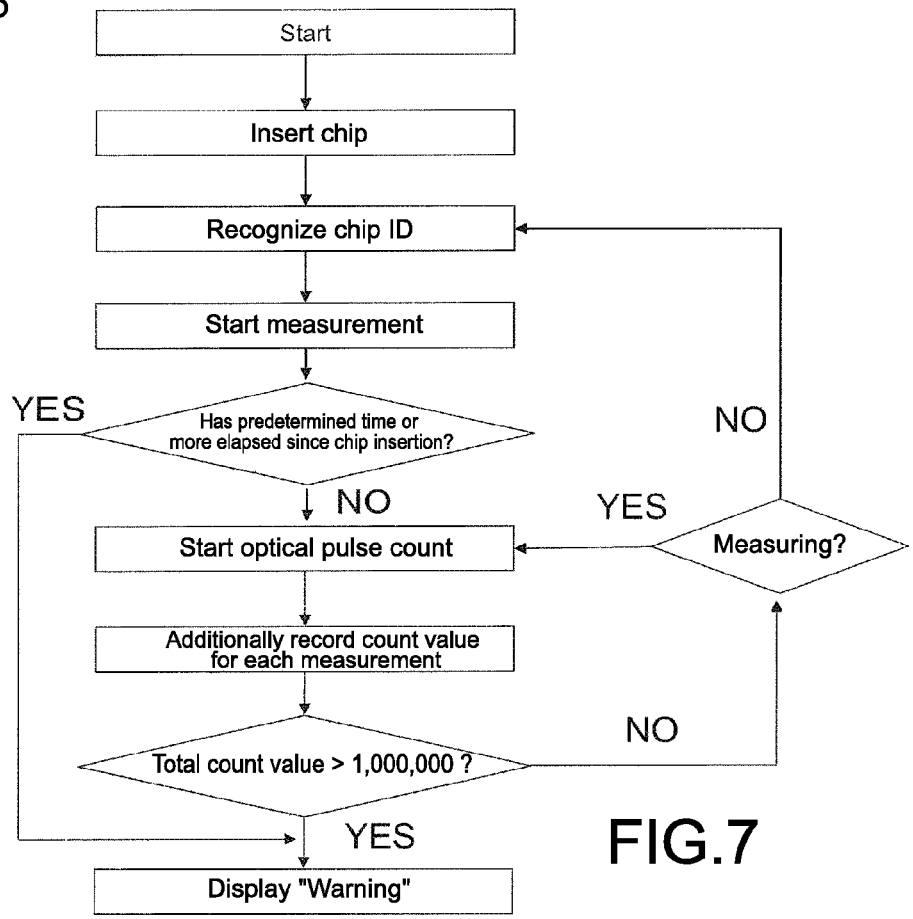
FIG. 7 is a flowchart showing a flow 5 of the chip lifetime judgment method according to the embodiment of the present disclosure.

Further, as an example, the judgment portion 13 checks the chip information (chip ID etc.) after the chip is inserted as shown in FIG. 7, and when a predetermined time has not elapsed (NO), starts the optical pulse count. When the predetermined time has elapsed since the chip insertion (YES), the judgment portion 13 judges that it is currently the chip exchange period without starting the optical pulse count and displays the "warning" on the display portion. The mounting time after the chip insertion may be stored in the storage portion 28 with time.

Whether the mounting time after the chip insertion is smaller than the predetermined time may be judged either by the judgment portion 13 or the chip information recognition portion 14. The result of the chip information recognition portion 14 may be transmitted to the judgment portion 13 so that the judgment portion 13 displays the "warning" or judges whether it is still "measuring".

<3. Flow Cytometer>

Owing to its high accuracy, the optical measurement apparatus of the present disclosure can be preferably used in a flow cytometer.

The "flow cytometry" is an analysis technique that analyzes and dispenses microparticles (samples S) by pouring microparticles as an analysis target in a fluid while the particles are aligned, and detecting fluorescent light or scattering light emitted from the microparticles when irradiated with laser light or the like. The process of the flow cytometry can be roughly classified into the following (1) water stream system, (2) optical system, (3) electric/analysis system, and (4) dispensing system.

(1) Water Stream System

In the water stream system, microparticles to be analyzed are arranged in a line in a flow cell (flow path). More specifically, a sheath flow is caused to flow in the flow cell at a constant flow rate, and a sample flow including the microparticles is injected into a center portion of the flow cell in that state. At this time, by a principle of a laminar flow, those flows are not mixed, and a laminar flow is formed. Then, the flow amounts of the sheath flow and the sample flow are adjusted based on the size of the microparticles to be analyzed so that the microparticles flow in a line.

(2) Optical System

In the optical system, light such as laser light is irradiated onto the microparticles to be analyzed, and fluorescent light or scattering light emitted from the microparticles is detected. While the microparticles are caused to pass the light irradiation portion while arranged in a line in the (1) water stream system, fluorescent light or scattering light emitted from the microparticle every time one microparticle passes is detected by an optical detector for each parameter, to thus analyze characteristics of each microparticle.

(3) Electric/Analysis System

In the electric/analysis system, the optical information detected by the optical system is converted into an electric signal. The electric signal obtained by the conversion is AD-converted so that a histrogram is extracted and analyzed by an analysis computer and software based on the obtained data.

For example, in a pulse detection system, an analysis is conducted by detecting, as an electric pulse, fluorescent light or scattering light that is caused when the microparticles cross laser light and analyzing a pulse height, pulse width, pulse area, and the like.

(4) Dispensing System

In the dispensing system, the microparticles that have been measured are separated and retrieved. As a typical dispensing method, there is a dispensing method including applying a plus or minus charge to microparticles that have been measured and sandwiching a flow cell with two deflection plates having a potential difference so that the charged microparticles are drawn to one of the deflection plates according to their charges.

It should be noted that the present disclosure may also take the following structures.

(1) A chip lifetime judgment apparatus, including:
    a light irradiation portion configured to irradiate light onto a sample flowing through a flow path in a detachable chip;
    a light detection portion configured to detect optical information emitted from the sample when irradiated with the light by the light irradiation portion; and
    a judgment portion configured to judge an exchange period of the chip based on the optical information detected by the light detection portion.

(2) The chip lifetime judgment apparatus according to (1), further including
    a chip information recognition portion configured to identify chip information from an identifier,
    in which the judgment portion judges the exchange period of the chip based on at least one of the optical information and the chip information.

(3) The chip lifetime judgment apparatus according to (1) or (2),
    in which the optical information is selected based on a threshold value.

(4) The chip lifetime judgment apparatus according to any one of (1) to (3),
    in which the judgment portion judges that it is currently the exchange period of the chip when the number of samples calculated based on the optical information reaches a constant value of a maximum count number.

(5) The chip lifetime judgment apparatus according to any one of (1) to (4),
    in which the judgment portion judges that it is currently the exchange period of the chip when a certain time has passed since it is judged that a large amount of samples have been measured at the same time based on the optical information.

(6) The chip lifetime judgment apparatus according to any one of (1) to (5),
    in which the judgment portion judges that it is currently the exchange period of the chip when a size of the sample calculated based on the optical information reaches a constant value of a maximum integration value for the sample size.

(7) An optical measurement apparatus, including the chip lifetime judgment apparatus according to any one of (1) to (6).

(8) A chip lifetime judgment method, including:
    irradiating light onto a sample flowing through a flow path in a detachable chip;
    detecting optical information emitted from the sample when irradiated with the light; and
    judging an exchange period of the chip based on the detected optical information.

(9) The chip lifetime judgment method, further comprising
    recognizing, by a chip information recognition portion, chip information from an identifier of the chip,
    in which the exchange period of the chip is judged based on at least one of the optical information and the chip information.

(10) The chip lifetime judgment method according to (8) or (9),
    in which the optical information is selected based on a threshold value.

(11) The chip lifetime judgment method according to any one of (8) to (10),
    in which it is judged that it is currently the exchange period of the chip when the number of samples calculated based on the optical information reaches a constant value of a maximum count number.

(12) The chip lifetime judgment method according to any one of (8) to (11),
    in which it is judged that it is currently the exchange period of the chip when a certain time has passed since it is judged that a large amount of samples have been measured at the same time based on the optical information.

(13) The chip lifetime judgment method according to any one of (8) to (12),
    in which it is judged that it is currently the exchange period of the chip when a size of the sample calculated based on the optical information reaches a constant value of a maximum integration value for the sample size.

(14) A program that executes the chip lifetime judgment method according to any one of (8) to (13).

Embodiment

Figure 10:
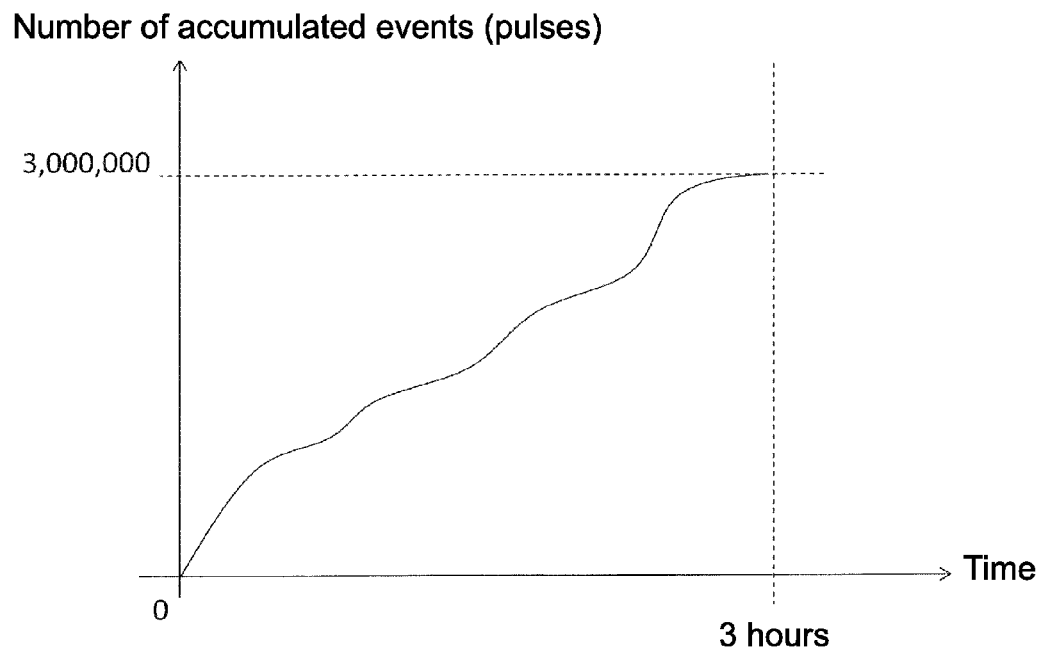
FIG. 10 is a graph showing the number of accumulated events (pulse signal etc.) in a case where 10,000 event per sec*60 sec*5 times is a lifetime per chip.

FIG. 10 is a graph showing a result of the number of accumulated events (pulse signals etc.) in a case where an unused microchip is mounted on a flow cytometer and 10,000 eps*60 sec*5 times is set as a lifetime (exchange period).

According to the technique of optically detecting a sample flowing through a flow path in the present disclosure, a lifetime of a chip including the flow path can be judged without relying on experiences or instinct of a user. Thus, an analysis accuracy can be maintained at a certain level or more. By using such a technique, it becomes possible to contribute to improvements in analysis techniques in various fields such as a medical field (pathology, tumor immunology, transplantation, genetics, regenerative medicine, chemotherapy, etc.), a drug development field, a clinical examination field, a food field, an agriculture field, an engineering field, a forensic medicine field, and a criminal identification field.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An optical measurement apparatus, comprising:
   a light irradiation portion configured to irradiate light onto a sample flowing through a flow path in a detachable chip;
   a light detection portion configured to detect optical information emitted from the sample when irradiated with the light by the light irradiation portion; and
   a judgment portion configured to judge an exchange period of the chip based on the optical information detected by the light detection portion.

2. The optical measurement apparatus according to claim 1, further comprising
   a chip information recognition portion configured to recognize chip information from an identifier,
   wherein the judgment portion judges the exchange period of the chip based on at least one of the optical information and the chip information.

3. The optical measurement apparatus according to claim 1,
   wherein the optical information is selected based on a threshold value.

4. The optical measurement apparatus according to claim 3,
   wherein the judgment portion judges that it is currently the exchange period of the chip when the number of samples calculated based on the optical information reaches a constant value of a maximum count number.

5. The optical measurement apparatus according to claim 3,
   wherein the judgment portion judges that it is currently the exchange period of the chip when a certain time has passed since it is judged that a large amount of samples have been measured at the same time based on the optical information.

6. The optical measurement apparatus according to claim 3,
   wherein the judgment portion judges that it is currently the exchange period of the chip when a size of the sample calculated based on the optical information reaches a constant value of a maximum integration value for the sample size.

7. A chip lifetime judgment method, comprising:
   irradiating light onto a sample flowing through a flow path in a detachable chip;
   detecting optical information emitted from the sample when irradiated with the light; and
   judging an exchange period of the chip based on the detected optical information.

* * * * *